United States Patent
O'Dell et al.

(10) Patent No.: US 10,067,071 B2
(45) Date of Patent: Sep. 4, 2018

(54) ANALYTE SPATIAL DETECTION SYSTEMS AND METHODS

(71) Applicant: FLIR Systems, Inc., Wilsonville, OR (US)

(72) Inventors: Brian D. O'Dell, Stillwater, OK (US); Robert K. Shelton, Stillwater, OK (US); Vu L. Nguyen, Goleta, CA (US)

(73) Assignee: FLIR Systems, Inc., Wilsonville, OR (US)

( * ) Notice: Subject to any disclaimer, the term of this patent is extended or adjusted under 35 U.S.C. 154(b) by 0 days.

(21) Appl. No.: 15/479,710

(22) Filed: Apr. 5, 2017

(65) Prior Publication Data
US 2017/0292917 A1 Oct. 12, 2017

Related U.S. Application Data

(60) Provisional application No. 62/320,366, filed on Apr. 8, 2016.

(51) Int. Cl.
*G01N 21/94* (2006.01)
*G01N 21/88* (2006.01)
*G08B 5/36* (2006.01)

(52) U.S. Cl.
CPC ......... *G01N 21/94* (2013.01); *G01N 21/8806* (2013.01); *G08B 5/36* (2013.01); *G01N 2021/945* (2013.01)

(58) Field of Classification Search
CPC ......... G01N 2021/945; G01N 21/8806; G01N 21/94; G08B 5/36
See application file for complete search history.

(56) References Cited

U.S. PATENT DOCUMENTS

| 4,835,688 A * | 5/1989 | Kimura ................. G06T 11/008 345/424 |
| 5,281,826 A | 1/1994 | Ivancic et al. |

(Continued)

OTHER PUBLICATIONS

Lee et al., "Efficient image segmentation of walking hazards using IR illumination in wearable low vision aids", Proceedings of the 6th International Symposium on Wearable Computers (ISWC'02), 2002, 2 pages, IEEE Computer Society, Piscataway, New Jersey.

(Continued)

*Primary Examiner* — Marcus Taningco
(74) *Attorney, Agent, or Firm* — Haynes and Boone, LLP

(57) ABSTRACT

Techniques are disclosed for systems and methods to provide reliable analyte spatial detection systems. An analyte spatial detection system includes an imaging module, a visible light projector, associated processing and control electronics, and, optionally, orientation and/or position sensors integrated with the imaging module and/or the visible light projector. The imaging module includes sensor elements configured to detect electromagnetic radiation in one or more selected spectrums, such as infrared, visible light, and/or other spectrums. The visible light projector includes one or more types of projectors configured project visible light within a spatial volume monitored by the imaging module. The system may be partially or completely portable and/or fixed in place. The visible light projector is used to indicate presence of a detected analyte on a surface near or adjoining the spatial position of the detected analyte.

20 Claims, 6 Drawing Sheets

(56) References Cited

U.S. PATENT DOCUMENTS

| | | | |
|---|---|---|---|
| 6,008,492 A | 12/1999 | Slater et al. | |
| 6,812,846 B2 | 11/2004 | Gutta et al. | |
| 9,438,869 B2* | 9/2016 | Gillies | A61B 5/055 |
| 9,704,267 B2* | 7/2017 | Kim | G06T 7/70 |
| 2005/0128184 A1* | 6/2005 | McGreevy | A61B 18/1206 345/156 |
| 2011/0157486 A1* | 6/2011 | Murata | G08B 7/062 348/744 |
| 2011/0183732 A1 | 7/2011 | Block et al. | |
| 2012/0075464 A1 | 3/2012 | Derenne et al. | |
| 2014/0168427 A1 | 6/2014 | Argue et al. | |
| 2016/0262243 A1* | 9/2016 | Kishimoto | H04N 9/3155 |
| 2016/0306062 A1* | 10/2016 | Keene | G01R 33/288 |

OTHER PUBLICATIONS

"Wet Switch® Flood Detector", DIVERSITECH, Jul. 15, 2015, 5 pages [online], [retrieved on Apr. 25, 2017]. Retrieved from the Internet: <URL:http://www.diversitech.com/Product-Line?id=a0jC0000005QGAkIAO>.

"Use on the floor to detect the presence of water or liquid. The sensor is accurate enough to measure distilled water", AlertWerks™ Rope Water Sensors, Black Box Network Services, Jul. 15, 2015, 2 pages [online], [retrieved on Apr. 25, 2017]. Retrieved from the Internet: <URL: http://ftp.blackbox.com/manuals/E/emerw-020_rev1.pdf>.

"What are viable approaches to a circuit to detect wet/moist cloth (bed-wetting)?", Electrical Engineering, Jul. 15, 2015, 4 pages [online], [retrieved on Apr. 25, 2017]. Retrieved from the Internet <URL:https://electronics.stackexchange.com/questions/28483/what-are-viable-approaches-to-a-circuit-to-detect-wet-moist-cloth-bed-wetting>.

"The Water Alarm Protects Your Property From Water Damage Wherever It Happens!", Gizmode® Innovations, Jul. 15, 2015, 3 pages [online], [retrieved on Apr. 25, 2017]. Retrieved from the Internet: <URL: http://www.thewateralarm.com/>.

"Wet floor detection", bing.com, Jul. 15, 2015, 3 pages [online], [retrieved on Apr. 25, 2017]. Retrieved from the Internet: <URL:https://www.bing.com/search?d=wet+floor+detection&qo=Submit&qs=n&form=QBLH&pg=wet+floor+detection&sc=2-19&sp=1&sk=&cvid=6a45fe5687b44eb081d5e3e748ccf127>.

"Wet floor detection", bing.com, Jul. 15, 2015, 3 pages [online], [retrieved on Apr. 25, 2017]. Retrieved from the Internet: <URL:https://www.bing.com/search?q=wet+floor+detection&go=Submit&qs=n&pg=wet+floor+detection&sc=2-19&sp=-1&sk=&cvid=6a45fe5687b44eb081d5e3e748ccf127&first=15&FORM=PORE>.

* cited by examiner

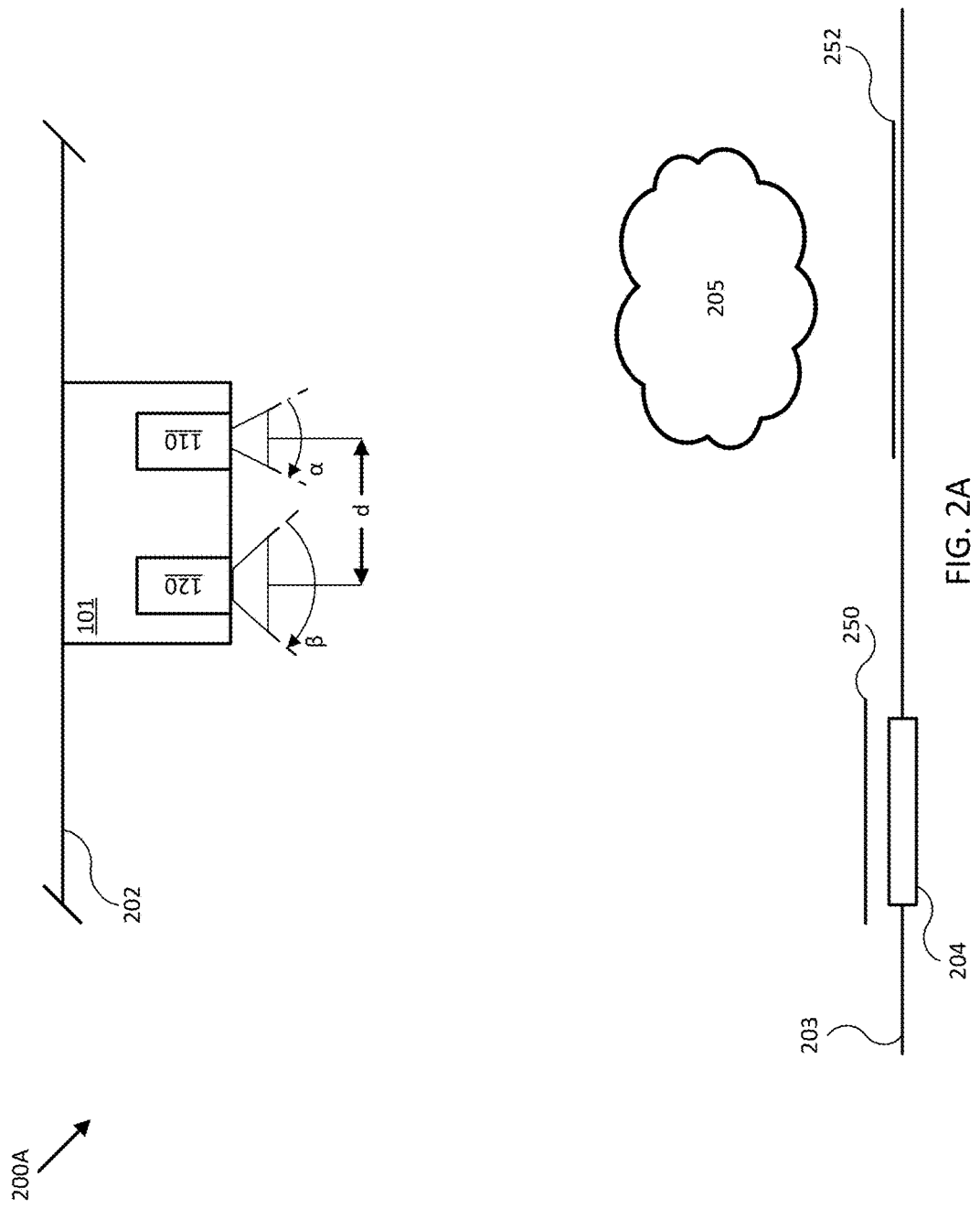

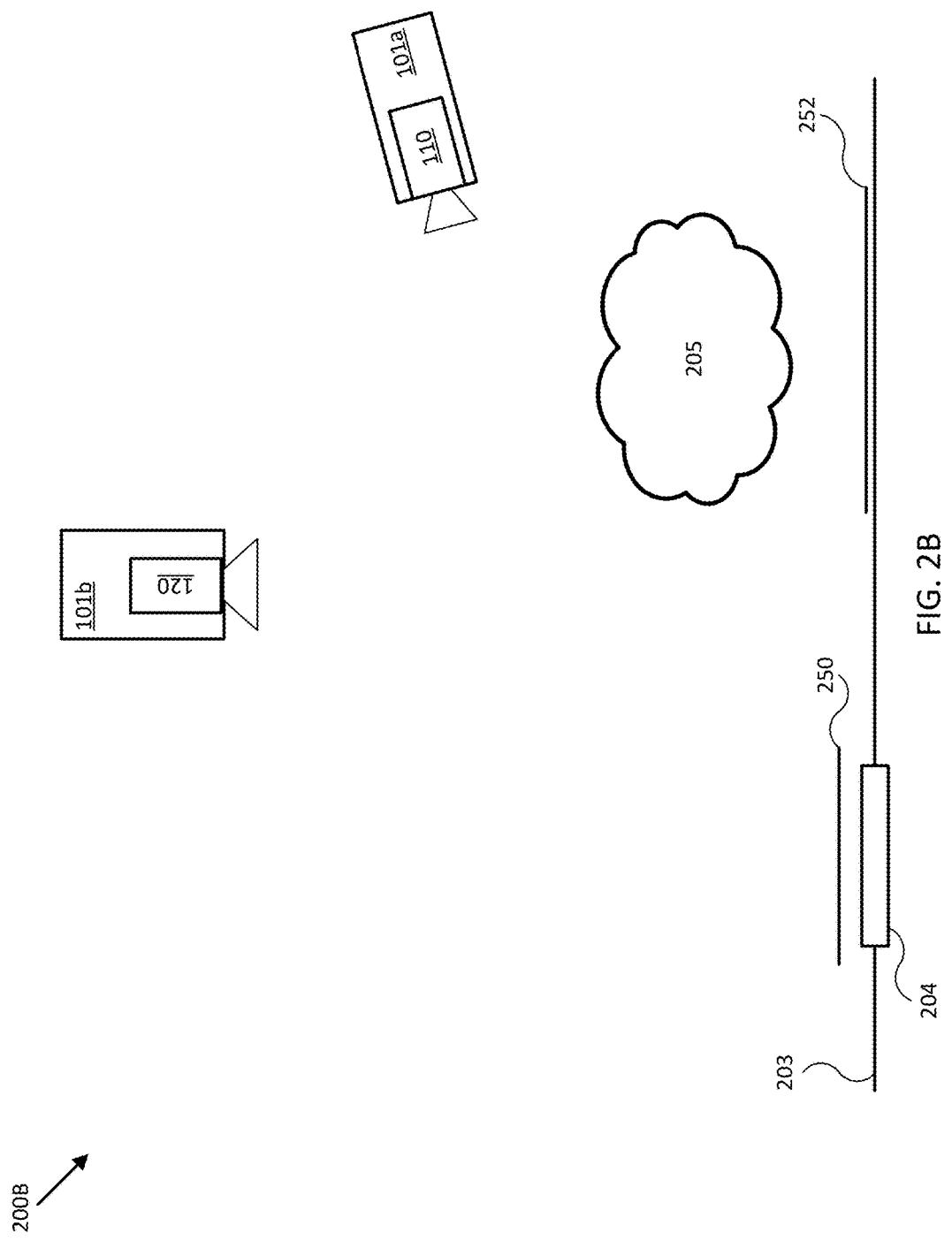

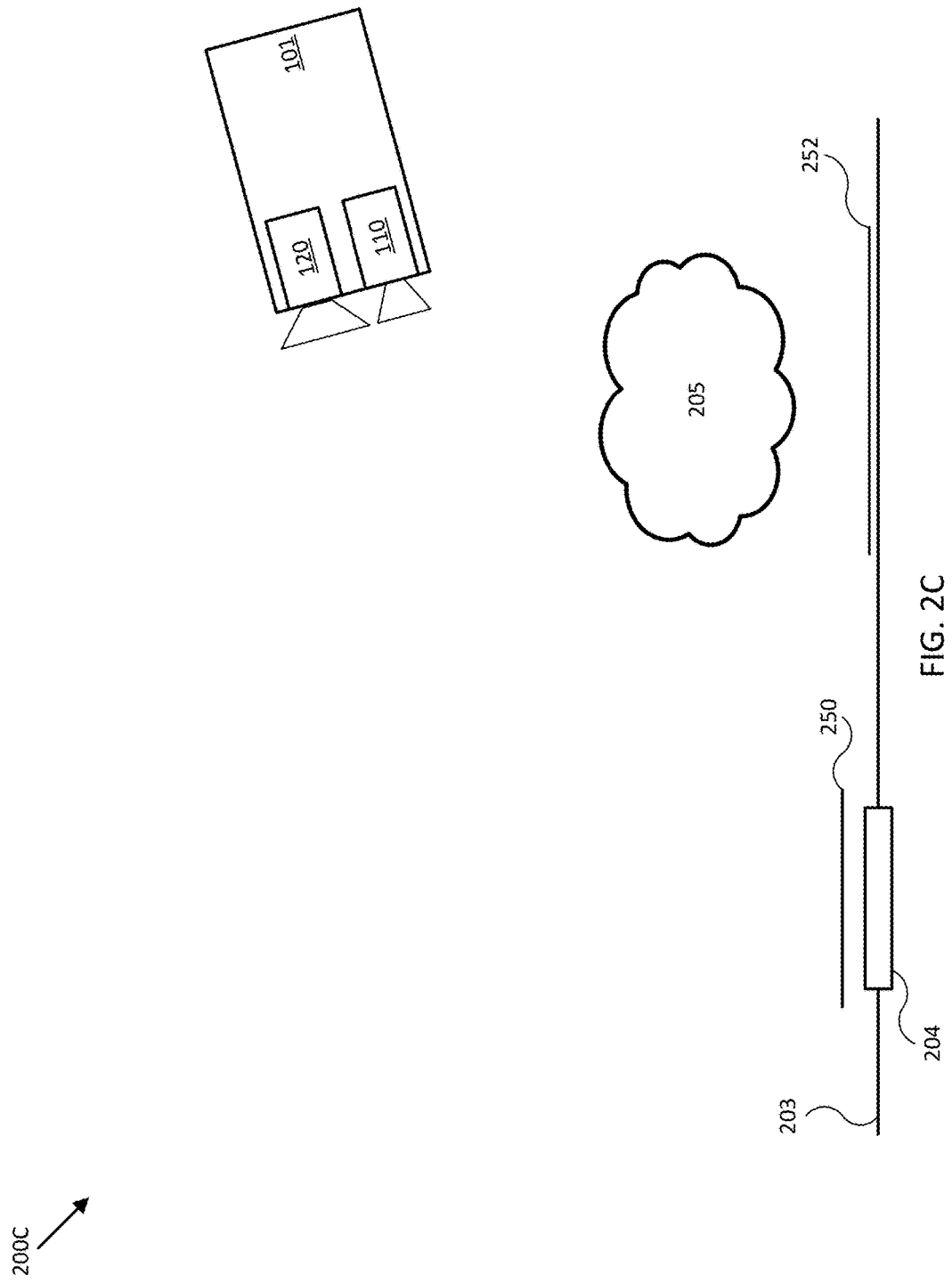

ANALYTE SPATIAL DETECTION SYSTEMS AND METHODS

CROSS-REFERENCE TO RELATED APPLICATIONS

This application claims priority to and the benefit of U.S. Provisional Patent Application No. 62/320,366 filed Apr. 8, 2016 and entitled "ANALYTE SPATIAL DETECTION SYSTEMS AND METHODS," which is incorporated herein by reference in its entirety.

GOVERNMENT LICENSE RIGHTS

This invention was made in part with government support under Contract Number W911SR-14-C-0035 awarded by the Joint Project Manager for Nuclear, Biological and Chemical Contamination Avoidance. The government has certain rights in the invention.

TECHNICAL FIELD

One or more embodiments of the invention relate generally to analyte detection systems and more particularly, for example, to systems and methods for providing spatially correlated visible indication of detected analytes.

BACKGROUND

Timely detection of chemical compounds or analytes can help protect workers and members of the public from harm. For example, timely detection of a water spill on the floor of a grocery store can significantly reduce a risk of slip and fall lawsuits or at least help fairly quantify resulting damages by providing a record of how long the water was on the floor before a member of the public slipped and fell. In another example, timely detected degassing from explosives or detection of the explosives themselves can significantly reduce a risk to anyone in the vicinity.

Unfortunately, conventional analyte detection systems are often unable to cover a wide area at once and are unable to provide accurate spatial information about where the analyte is within a monitored area, which can cause further harm to the public or a worker by inadvertently herding them towards danger or wasting critical time while an expert physically manipulates or interprets the detection result to find or confirm the presence of the analyte and address the harmful condition caused by the presence of the analyte. Thus, there is a need for an improved methodology to provide a reliable and flexible analyte spatial detection system that can reduce risk of harm yet not unnecessarily impede typical operations.

SUMMARY

Techniques are disclosed for systems and methods to provide accurate analyte spatial detection systems. An analyte spatial detection system may include an imaging module, a visible light projector, associated processing and control electronics, and, optionally, orientation and/or position sensors integrated with the imaging module and/or the visible light projector. The imaging module may include one or more sensor elements (e.g., one or more focal plane arrays of sensor elements or pixels) each configured to detect electromagnetic radiation in one or more selected spectrums, such as infrared, visible light, and/or other spectrums. The visible light projector may include one or more of a scanning laser projector, a digital projector, an array of light emitting diodes, a directed light source, and/or other types of projectors configured to generate visible light and project it within a spatial volume monitored by the imaging module. The system may be partially or completely portable or fixed in place. The visible light projector may be used to indicate presence of a detected analyte on a surface near or adjoining the spatial position of the detected analyte. Resulting projected analyte indicators may be accompanied with audible alarms and/or electronic notifications sent remotely over a network. Such electronic notifications may indicate the presence, composition, temperature, and/or other physical properties or characteristics of the analyte, the associated environmental conditions, and/or system 101.

In various embodiments, an analyte spatial detection system may include an orientation sensor, a position sensor, a gyroscope, an accelerometer, and/or one or more additional sensors, actuators, controllers, user interfaces, mapping systems, and/or other modules integrated with or disposed in proximity to the system. Each component of the system may be implemented with a logic device adapted to form one or more wired and/or wireless communication links for transmitting and/or receiving sensor signals, control signals, or other signals and/or data between the various components.

In one embodiment, a system may include an imaging module configured to image a spatial volume for electromagnetic radiation in a selected spectrum; a visible light projector configured to general visible light and project it within the spatial volume; and a logic device configured to communicate with the imaging module and the visible light projector. The logic device may be configured to receive image data corresponding to the spatial volume from the imaging module; process the received image data to detect presence and spatial extents of an analyte within the spatial volume; and control the visible light projector to project an analyte indicator on a surface within the spatial volume, wherein the projected analyte indicator is configured to indicate the spatial extents of the analyte.

In another embodiment, a method may include receiving image data corresponding to a spatial volume imaged by an imaging module; processing the received image data to detect presence and spatial extents of an analyte within the spatial volume; and projecting an analyte indicator on a surface within the spatial volume, wherein the analyte indicator is configured to indicate the spatial extents of the analyte.

The scope of the invention is defined by the claims, which are incorporated into this section by reference. A more complete understanding of embodiments of the invention will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

FIG. 2A illustrates a diagram of an analyte spatial detection system in accordance with an embodiment of the disclosure.

FIG. 2B illustrates a diagram of an analyte spatial detection system in accordance with an embodiment of the disclosure.

FIG. 2C illustrates a diagram of an analyte spatial detection system in accordance with an embodiment of the disclosure.

Embodiments of the invention and their advantages are best understood by referring to the detailed description that follows. It should be appreciated that like reference numerals are used to identify like elements illustrated in one or more of the figures.

DETAILED DESCRIPTION

In accordance with various embodiments of the present disclosure, reliable and informative analyte spatial detection systems and methods may advantageously include a controller, an imaging module, and a visible light projector. For example, the controller may be configured to detect a presence and/or spatial extents of an analyte in image data provided by the imaging module, and the controller may be configured to project an analyte indicator to provide human-visible indication the spatial extents of the analyte, substantially in real time. Such system may optionally include an orientation sensor, a gyroscope, an accelerometer, and/or a position sensor, configured to provide measurements of an orientation and/or a position of the imaging module and/or the visible light projector to help facilitate accurately projecting the analyte indicator to indicate the spatial extents of the analyte. For example, the sensors may be mounted to or within a housing for the system, or may be integrated with the imaging module and/or the visible light projector. In other embodiments, the imaging module and/or the visible light projector may be fixed in relation to a monitored scene and/or each other, and the optional sensors may be omitted and/or substituted with known values for the positions and/or orientations.

Embodiments of the present disclosure can reliably spatially detect and produce accurate warnings for the presence of liquid, solid, and/or gaseous analytes within a spatial volume monitored by the imaging module. By projecting the spatially delineated warnings within the monitored volume (e.g., on a surface of a floor or other surface within the monitored volume), embodiments inherently provide an indication for a member of the public or a worker to avoid the danger presented by the analyte and/or to accurately assess and resolve the danger (e.g., to remove the analyte), substantially in real time.

Alternative systems that provide analyte indicators on a monitor or even a display of a portable electronic device cannot provide as direct and accurate indication of the analyte, particularly to members of the public who may not have immediate access to a display, which can lead to accidental harm (e.g., stampedes, misdirection due to incorrect interpretation of the indicators and the actual position of the analyte, and/or other harms caused by inaccurate and/or unreliable communication of the danger to someone within the monitored volume). Moreover, less accurate and less direct systems typically result in larger responses than necessary (e.g., closing of a large portion of a public area due to a relatively small amount of analyte incursion), which can unnecessarily harm general productivity related to the monitored volume and, potentially, relatively large adjacent areas.

Figure 1:
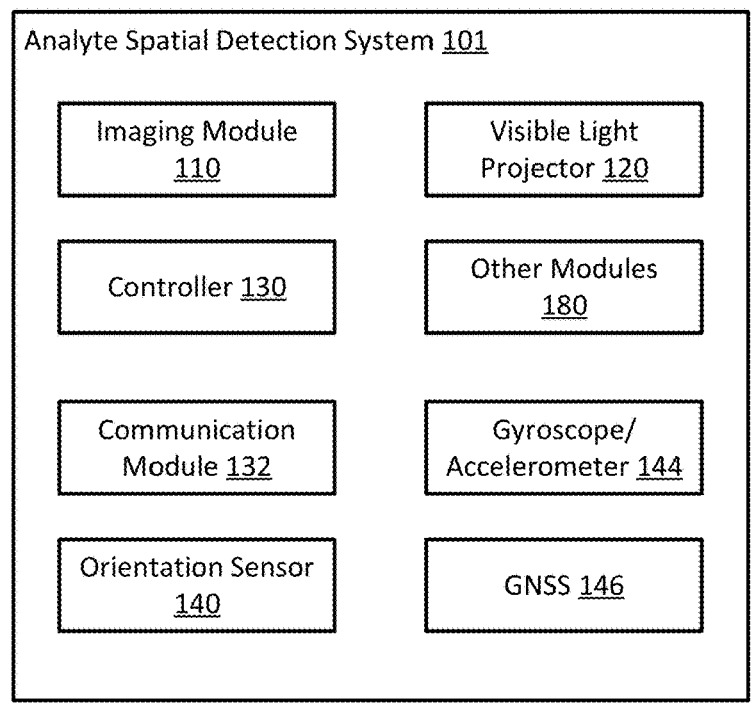
FIG. 1 illustrates a block diagram of an analyte spatial detection system in accordance with an embodiment of the disclosure.
Figure 3A:
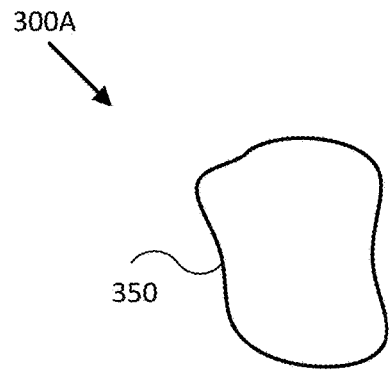
FIGS. 3A-D illustrate diagrams of projected analyte indicators generated by an analyte spatial detection system in accordance with embodiments of the disclosure.
Figure 3B:
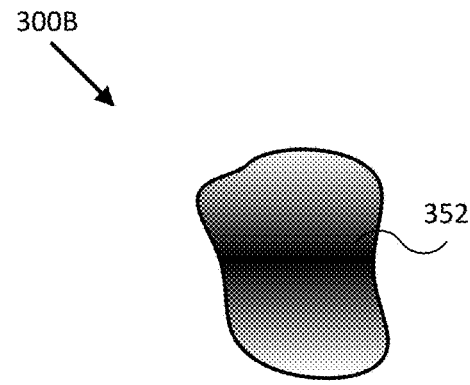
Figure 3C:
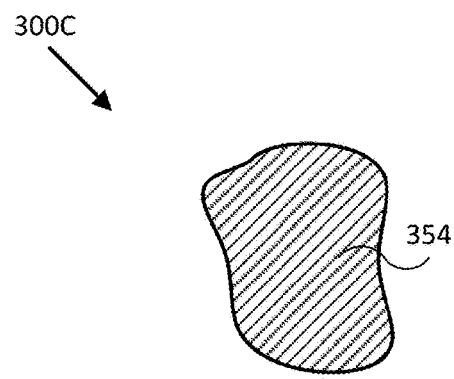
Figure 3D:
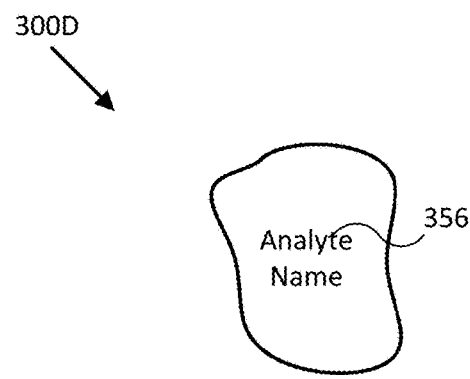

FIG. 1 illustrates a block diagram 100 of an analyte spatial detection system 101 in accordance with an embodiment of the disclosure. In various embodiments, system 101 may be configured to capture image data corresponding to a monitored spatial volume. System 101 may then use this data detect a presence and/or spatial extents of an analyte within the spatial volume. After the presence and/or spatial extents of the analyte are determined, system 101 may project an analyte indicator on a surface within the spatial volume, such as on various object surfaces within the spatial volume (e.g., on the ground, on a floor, on an object on the ground or floor), and/or on an analyte surface, such as a liquid or gaseous form (e.g., that at least partially reflects visible light) above the ground or floor or other object surface, to warn someone within the spatial area of the presence and spatial extents of the analyte.

Detected analytes may include solids, liquids, and/or gasses, and may include any chemical compound that can be detected by an imaging module, as described herein. For example, water, gasoline, coolant, oil, acid, cooking gas, nitrogen, oxygen, various human-poisonous gasses, various explosives (e.g., TNT), chemical weapons, oxidizers (e.g., nitrates, chlorates, perchlorates), toxic industrial chemicals, and/or other analytes may be detected by an imaging module, with or without active illumination to encourage florescence and/or other analyte responses that can be imaged by an imaging module. Projected analyte indicators may be accompanied by other indicators, such as audible indicators and/or electronic communications or alerts communicated over a network, such as a wired or wireless communication network.

In the embodiment shown in FIG. 1, system 101 includes imaging module 110, visible light projector 120, controller 130, communication module 132, orientation sensor 140, gyroscope/accelerometer 144, global navigation satellite system (GNSS) 146, and other modules 180. In other embodiments, one or more of communication module 132, orientation sensor 140, gyroscope/accelerometer 144, and/or GNSS 146 may be omitted as unnecessary, such as when absolute and/or relative positions of imaging module 110 and/or visible light projector 120 are fixed and/or known. In some embodiments, controller 130 may be integrated with imaging module 110 and/or projector 120.

Imaging module 110 may be implemented as one or more sensor elements (e.g., one or more focal plane arrays (FPAs) of sensor elements or pixels, such as in a camera) each configured to detect electromagnetic radiation in one or more selected spectrums, such as infrared, visible light, and/or other spectrums (e.g., bands of substantially continuous ranges of wavelengths of electromagnetic radiation), spatially, so as to produce image data corresponding to a spatial volume monitored by imaging module 110. For example, the one or more spectrums may be selected to enable detection of a particular analyte, phase (e.g., solid, liquid, gas), temperature, concentration, or flow/motion directions of an analyte.

In one embodiment, flow or motion direction of a detected analyte may be determined by detecting or determining a concentration distribution of an analyte within a volume and/or at boundaries of the analyte, for example, and determining one or more rates of diffusion of the analyte from relatively high to relatively low concentrations within the concentration distribution. For example, the concentration distribution may be based on the spatially localized intensity of the detected spectrum of the analyte (e.g., where higher spatially localized intensities correspond to higher concentrations of the detected analyte), and the one or more rates of diffusion may be based on a temperature of the analyte and/or surrounding medium In various embodiments, such sensor elements may be implemented with one or more microbolometers, thermopiles, quantum well infrared photodetectors (e.g., including lattice matched and/or strained layer superlattice based photodetectors), InGaAs based photodetectors, HgCdTe based photodetectors, imaging Raman spectrometer assemblies, complementary metal-oxide semiconductor (CMOS) sensors, near infrared (NIR) sensors, silicon photomultipliers, hyperspectral imagers, multispectral imagers, thermographic imagers, and/or other sensor and/or sensor element technologies that may be used to image a spatial volume according to one or more selected spectrums, such as terahertz, x-ray, ultraviolet, visible, infrared (e.g., near infrared, short wave infrared, medium wave infrared, and/or long wave infrared), and/or other spectrums.

In some embodiments, imaging module 110 may include an infrared FPA and a visible light FPA configured to image the same spatial volume, for example, to facilitate multiple spectrum (e.g., visible light and infrared) combined image processing and/or to facilitate detection of a projected analyte indicator within the spatial volume (e.g., to provide feedback to correct or update a size or shape of a projected analyte indicator). Such combined image processing may include, for example, extracting relatively high spatial frequency information from a visible spectrum image and generating a combined image by overlaying or blending the extracted high spatial frequency visible spectrum information onto/with an infrared image, where the infrared image and/or the high spatial frequency visible spectrum information are scaled, rotated, and/or otherwise processed such that the high spatial frequency visible spectrum information is properly registered to (e.g., spatially scaled and/or aligned with) the infrared image. In various embodiments, imaging module 110 may be used in combination with one or more active or passive filters modules (e.g., band pass filters) and/or active illumination modules (e.g., elements of other modules 180) to facilitate imaging of the spatial volume according to a particular set of selected spectrums and/or to facilitate detection of a particular analyte.

Visible light projector 120 may be implemented as one or more of a scanning laser projector, a digital projector, an array of light emitting diodes, a mechanical or fixed directed light source, and/or other types of projectors configured to generate visible light and project it within a spatial volume monitored by the imaging module. For example, in one embodiment, visible light projector 120 may be implemented as a scanning light projector (e.g., implemented with a laser or a substantially calumniated light source) and be configured to project an outline and/or other analyte indicator structures on the surface of a floor, a table, a cloud of mist, and/or other solid, liquid, or gaseous object within the monitored volume. In another embodiment, visible light projector 120 may be implemented as a digital projector (e.g., liquid crystal display, digital light processing, and/or other type of digital projector) and be configured to project a multiple color/false color outline, intensity graph, and/or other analyte indicator structures on a surface within the monitored volume. In yet another embodiment, visible light projector 120 may be implemented as a multi-hue light bulb configured to provide a diffuse light within the monitored volume that primarily uses color and/or color intensity on all surfaces within the monitored volume as the analyte indicator. In various embodiments, projector 120 may be used to project other information, such as sensor, parameter, and/or control information related to operation of system 101, onto a surface within the monitored volume.

Controller 130 may be implemented as any appropriate logic device (e.g., processing device, microcontroller, processor, application specific integrated circuit (ASIC), field programmable gate array (FPGA), memory storage device, memory reader, or other device or combinations of devices) that may be adapted to execute, store, and/or receive appropriate instructions, such as software instructions implementing a control loop for controlling various operations of system 101, for example. Such software instructions may also implement methods for processing sensor signals, determining sensor information, providing feedback (e.g., through projector 120, communication module 132, and/or other modules 180), querying devices for operational parameters, selecting operational parameters for devices, or performing any of the various operations described herein (e.g., operations performed by logic devices of various devices of system 101).

In addition, a machine readable medium may be provided for storing non-transitory instructions for loading into and execution by controller 130. In these and other embodiments, controller 130 may be implemented with other components where appropriate, such as volatile memory, non-volatile memory, one or more interfaces, and/or various analog and/or digital components for interfacing with devices of system 101. For example, controller 130 may be adapted to store sensor signals, sensor information, parameters for coordinate frame transformations, calibration parameters, sets of calibration points, and/or other operational parameters, over time, for example, and provide such stored data to a user using projector 120, communication module 132, and/or other modules 180. In some embodiments, controller 130 may be integrated with imaging module 110 and/or visible light projector 120. As noted herein, controller 130 may be adapted to execute one or more control loops for mechanically actuated device control, projector control, and/or performing other various operations of system 101. In some embodiments, a control loop may include processing sensor signals and/or sensor information in order to control one or more operations of imaging module 110, visible light projector 120, and/or system 101.

Communication module 132 may be configured to facilitate communication and interfacing between various components of system 132, multiple embodiments of system 132, and/or a user interface, such as a smart phone or a personal computer (e.g., other components 180). For example, elements such as imaging module 110, visible light projector 120, sensors 140-146, and/or other components 180 may transmit and receive data to and from controller 130 through communication module 132, which may manage wired and/or wireless connections (e.g., through proprietary RF links, proprietary infrared links, and/or standard wireless communication protocols such as IEEE 802.11 WiFi standards and Bluetooth™) between the various components. Such wireless connections may allow imaging module 110 and/or visible light projector 120 to be mounted where it would not be convenient to provide wired connections, for example.

Communication module 132 may be further configured to allow components of system 101 to communicate and interface with other components of a monitoring system monitoring the spatial volume. For example, controller 130 may communicate, via communication module 132, with a motion detector, smoke detector, and other existing sensors and electronic components. In this regard, communication module 132 may support various interfaces, protocols, and standards for networking, such as the controller area network (CAN) bus, the local interconnect network (LIN) bus, the media oriented systems transport (MOST) network, or the ISO 11738 (or ISO bus) standard. Furthermore, communication module 132 may be configured to send control signals generated by controller 130 using these interfaces and protocols.

In some embodiments, system 4000 may include a number of communication modules 132 adapted for various applications of system 101 with respect to various types of spatial volumes. In other embodiments, communication module 132 may be integrated into or implemented as part of various other components of system 101. For example, imaging module 110, visible light projector 120, and controller 130 may each comprise a subcomponent that may be configured to perform the operations of communication module 132, and may communicate with one another via wired and/or wireless connections without a separate communication module 132.

Orientation sensor 140 may be implemented as one or more of a compass, float, accelerometer, and/or other device capable of measuring an orientation of imaging module 110 and/or projector 120 (e.g., magnitude and direction of roll, pitch, and/or yaw, relative to one or more reference orientations such as gravity and/or Magnetic North) and providing such measurements as sensor signals that may be communicated to various devices of system 101. Gyroscope/accelerometer 144 may be implemented as one or more electronic sextants, semiconductor devices, integrated chips, accelerometer sensors, accelerometer sensor systems, or other devices capable of measuring angular velocities/accelerations and/or linear accelerations (e.g., direction and magnitude) of mobile structure 101 and providing such measurements as sensor signals that may be communicated to other devices of system 101 (e.g., controller 130). Such measurements may be used to determine or estimate, at least partially, an orientation and/or position of imaging module 110 and/or visible light projector 120. Gyroscope/accelerometer 144 may be positioned and/or adapted to make such measurements in relation to a particular coordinate frame of system 101, for example. In various embodiments, gyroscope/accelerometer 144 may be implemented in a common housing and/or module to ensure a common reference frame or a known transformation between reference frames.

GNSS 146 may be implemented as a global positioning satellite receiver and/or other device capable of determining absolute and/or relative position of mobile structure 101 based on wireless signals received from space-born and/or terrestrial sources (e.g., GPS, GLONASS), for example, and capable of providing such measurements as sensor signals that may be communicated to various devices of system 101. Using orientation and/or position information from orientation sensor 140, gyroscope/accelerometer 144, and/or GNSS 146, controller 130 may be able to determine a proper position for a projected analyte indicator within a spatial volume, relative to image data provided by imaging module 110.

Other modules 180 may include other and/or additional sensors, indicators (e.g., an alarm light to indicate a locally detected analyte, such as water on a floor imaged by imaging module 110), actuators, communications modules/nodes, and/or user interface devices used to provide additional environmental information of a spatial volume monitored by system 101, for example. In some embodiments, other modules 180 may include a rangefinder (e.g., linked with image sensor 110 and/or projector 120), a humidity sensor, a wind and/or water temperature sensor, a barometer, a radar system, a visible spectrum camera, an infrared camera, and/or other environmental sensors providing measurements and/or other sensor signals that can be displayed to a user and/or used by other devices of system 101 (e.g., controller 130) to provide operational control of system 101 that compensates for environmental conditions, such as environmental conditions affecting detection of a particular analyte, for example. In some embodiments, other modules 180 may include a power supply (e.g., a battery or transformer), power supply electronics, fixed active illumination, and/or one or more actuated devices (e.g., actuated active illuminators, spotlights, cameras, radars, sonars, and/or other actuated devices), controlled through use of one or more control signals (e.g., provided by controller 130), to help alert people to a detected analyte and/or to help detect a particular analyte. In various embodiments, other modules 180 may include a clock or timer configured to measure absolute times and/or time periods associated with an analyte detection event, such as a start, duration, and/or end of an analyte detection event.

Other modules 180 may also include one or more active or passive filters modules and/or active illumination modules configured to facilitate imaging of a spatial volume according to a particular set of selected spectrums and/or to facilitate detection of a particular analyte (e.g., be excluding certain wavelengths of electromagnetic radiation and/or other noise sources, for example). In other embodiments, other modules 180 may include one or more user interfaces configured to allow a user to select particular spectrums and/or analytes for detection, for example, to enable or disable types of projected analyte indicators and/or indicator structures, shapes, sizes, colors, and/or other attributes.

For example, other modules 180 may include a personal computing device (e.g., a smart phone or personal computer) enabling a user to determine and/or control an operational state of system 101 and/or elements of system 101, including viewing image data provided by imaging module 110, detected analyte spatial extents determined by controller 130, and/or projected analyte indicator provided by projector 120. In various embodiments, such personal computing device may allow a user to configure an array of systems similar to system 101 to coordinate monitoring multiple differentiated spatial volumes substantially simultaneously (e.g., multiples of the spatial volume monitored by a single system 101), for example, or to monitor a single spatial volume with an increased spatial resolution. In embodiments with arrays of system 101, such coordination may include projecting analyte indicators configured to indicate one or more remotely detected analytes, to indicate variable levels of danger associated with one or more remotely detected analytes (e.g., colors and/or intensities indicating estimated concentration levels), to indicate an escape route and/or a safe navigation route avoiding one or more remotely detected analytes, and/or to provide other information related to one or more remotely detected analytes, as described herein.

Such user interfaces (e.g., as elements of other modules 180) may be implemented as a display, an indicator light, a touch screen, a keyboard, a mouse, a joystick, a knob, a button, and/or any other device capable of accepting user input and/or providing feedback to a user. In various embodiments, a user interface may be adapted to provide user input (e.g., as a type of signal and/or sensor information) to other devices of system 101, such as controller 130. A user interface may also be implemented with one or more logic devices that may be adapted to execute instructions, such as software instructions, implementing any of the various processes and/or methods described herein. For example, a user interface may be adapted to form communication links, transmit and/or receive communications (e.g., sensor signals, control signals, sensor information, user input, and/or other information), determine various coordinate frames and/or orientations, determine parameters for one or more coordinate frame transformations, and/or perform coordinate frame transformations, for example, or to perform various other processes and/or methods.

In various embodiments, a user interface (e.g., other modules 180) may be adapted to accept user input, for example, to form a communication link, to select a particular wireless networking protocol and/or parameters for a particular wireless networking protocol and/or wireless link (e.g., a password, an encryption key, a MAC address, a device identification number, a device operation profile, parameters for operation of a device, and/or other parameters), to select a method of processing sensor signals to determine sensor information, to adjust a position and/or orientation of an articulated sensor, and/or to otherwise facilitate operation of system 101 and devices within system 101. Once a user interface accepts a user input, the user input may be transmitted to other devices of system 101 over one or more communication links.

In one embodiment, a user interface may be adapted to receive a sensor or control signal (e.g., from imaging module 110 or orientation sensor 140) over communication links formed by one or more associated communication modules 132, for example, and display sensor and/or other information corresponding to the received sensor or control signal to a user. In related embodiments, a user interface may be adapted to process sensor and/or control signals to determine sensor and/or other information. In such embodiments, a user interface may be adapted to process the sensor signals to determine sensor information indicating an estimated and/or absolute roll, pitch, and/or yaw (attitude and/or rate), and/or a position or series of positions of elements of system 101, for example, and display the sensor information as feedback to a user. In one embodiment, a user interface may be adapted to display a time series of various sensor information and/or other parameters as part of or overlaid on a graph or map, which may be referenced to a position and/or orientation of elements of system 101. For example, a user interface may be adapted to display a time series of positions and/or orientations of imaging module 110 and/or visible light projector 120 overlaid on a geographical map, which may include one or more graphs indicating a corresponding time series of detected analytes, analyte spatial extents, sensor information, and/or other sensor and/or control signals.

Sensor signals, control signals, and other signals may be communicated among elements of system 101 using a variety of wired and/or wireless communication techniques, including voltage signaling, Ethernet, WiFi, Bluetooth, Zigbee, Xbee, Micronet, or other medium and/or short range wired and/or wireless networking protocols and/or implementations, for example. In such embodiments, each element of system 101 may include one or more modules supporting wired, wireless, and/or a combination of wired and wireless communication techniques.

In some embodiments, various elements or portions of elements of system 101 may be integrated with each other, for example, or may be integrated onto a single printed circuit board (PCB) to reduce system complexity, manufacturing costs, power requirements, and/or timing errors between the various sensor measurements. For example, imaging module 110, visible light projector 120, and controller 130 may be configured to share one or more components, such as a memory, a logic device, communications module 132, and/or other components, and such sharing may act to reduce and/or substantially eliminate such timing errors while reducing overall system complexity and/or cost.

FIG. 2A illustrates a diagram 200A of analyte spatial detection system 101 in accordance with an embodiment of the disclosure. In the embodiment shown in FIG. 2A, analyte spatial detection system 101 is implemented as a monolithic installation (e.g., where imaging module 120 and visible light projector 120 have fixed relative positions and/or orientations) fixed relative to a spatial volume (e.g., the lower portion of diagram 200A). For example, in some embodiments, diagram 200A could represent an industrial or retail spatial volume defined by ceiling 202 and floor or ground 203, and system 101 could be mounted to ceiling 202 in view of a portion of floor or ground 203.

Also shown in FIG. 2A are analytes 204 and 205 and projected analyte indicators 250 and 252. Analyte 204 may correspond to a liquid or solid analyte on or within floor 203, and analyte 205 may correspond to a gaseous analyte disposed above floor 203. System 101 may be configured to project analyte indicator 250 on floor 203 and/or analyte 204 to indicate presence and/or spatial extents of analyte 204, and/or to project analyte indicator 252 on floor 203 (or on analyte 205 if it is reflective of visible light) to indicate presence and/or spatial extents of analyte 205. For example, in embodiments where analyte 204 is water on floor 203 presenting a risk of slip and fall, system 101 may be configured to detect the water on floor 203 and project analyte indicator 250 in a visible light spectrum to indicate presence, spatial extents, and/or the estimated amount of water (e.g., using the intensity of the projected visible light, for example).

In FIG. 2A, imaging module 110 and visible light projector 120 are separated by distance d and may have different fields of view (indicated by view angles $\alpha$ and $\beta$). System 101 (e.g., controller 130) may be configured to determine any parallax or other spatial errors between the image data provided by imaging module 110 and visible light projector 120 and compensate for and/or correct such errors when projecting analyte indicators, as described herein. For example, with known values for d, $\alpha$, and $\beta$, controller 130 may be configured to calculate an exact compensation calibration for any projected analyte indicator 250 or 252, for any vertical distance between projector 120 and surface upon which analyte indicators 250 or 252 are projected. Such vertical distance may be measured using a range finder, for example, or by estimating the vertical distance based on focus parameters and/or other sensor information. In embodiments where d, $\alpha$, or $\beta$ are unknown, controller 130 may be configured to determine an estimated compensation calibration by using imaging module 110 to image both the detected analyte and the projected analyte indicator (e.g., in embodiments where imaging module 110 is able to image at least a portion of visible light).

FIG. 2B illustrates a diagram 200B of analyte spatial detection system 101 in accordance with an embodiment of the disclosure. In the embodiment shown in FIG. 2B, analyte spatial detection system 101 is implemented as a distributed installation (e.g., where imaging module 120 or visible light projector 120 is mobile or portable and they have variable relative positions and/or orientations) with one or both elements having a variable position and/or orientation relative to a spatial volume (e.g., the lower portion of diagram 200B, similar to that shown in FIG. 2A). For example, in some embodiments, diagram 200B could represent an outdoor industrial, retail, urban, or rural spatial volume with no upper bound and floor or ground 203 as the lower bound, and visible light projector 120 of portion 101b of system 101 could be mounted, posted, or flown above ground 203 in view of a portion of ground 203 to project analyte indicators 250 and 252, and imaging module 110 of portion 101a of system 101 could be held or scanned across the spatial volume to detect corresponding analytes 204 and 205.

FIG. 2C illustrates a diagram 200C of analyte spatial detection system 101 in accordance with an embodiment of the disclosure. In the embodiment shown in FIG. 2C, analyte spatial detection system 101 is implemented as a monolithic installation having a variable position and/or orientation relative to a spatial volume (e.g., the lower portion of diagram 200C). For example, in some embodiments, diagram 200C could represent a spatial volume that will be scanned by a portable embodiment of system 101 with floor or ground 203 as the lower bound, and imaging module 110 and visible light projector 120 of system 101 could be flown (e.g., using an unmanned aerial vehicle (UAV) sized to fit the spatial volume) walked, scanned, or held above ground 203 to detect analytes 204 and 205 and to project corresponding analyte indicators 250 and 252.

FIGS. 3A-D illustrate diagrams of respective projected analyte indicators 300A-D generated by analyte spatial detection system 101 in accordance with embodiments of the disclosure. In general, projected analyte indicators may be configured to indicate any one of a number of characteristics of a detected analyte, such as name or chemical formula, composition, chemical class (e.g., explosive, chemical weapon, strong oxidizer, water reactive, inert, and/or other chemical classes), temperature, phase, concentration, toxicity, and/or other analyte characteristics. In some embodiments, projected analyte indicators may be configured to indicate an appropriate method to decontaminate a volume or surface that has been contaminated with the detected analyte. Examples of such appropriate methods may include using a granulated absorber and/or a non-water-based solvent for a water reactive analyte, for example, or keeping a room or building substantially closed so as not to allow a highly toxic gas or liquid to escape the confines of an enclosed structure.

In additional embodiments, projected analyte indicators may include one or more graphics, codes, and/or other visible or textual symbols standardized by a government organization, such as the Department of Transportation, the Occupational Safety and Health Administration, the National Institute for Occupational Safety and Health (NIOSH), the Centers for Disease Control and Prevention, and/or other government or standards organizations, for example, that correspond to a detected analyte. Corresponding standardized libraries or guides of information related to the projected analyte indicators and/or detected analyte (e.g., NIOSH guides for Chemical Hazards, and/or other libraries or guides) may be transmitted to a user interface (e.g., other modules 180) for display by a user. Such standardized libraries and/or guides may include detailed and/or contextualized (e.g., for different environmental conditions) clean up, safety, and/or other mitigation strategies corresponding to a detected analyte. By incorporating such standardized graphics, codes, other visible or textual symbols, libraries, and/or guides, embodiments allow users to make quicker decisions about what mitigation strategies to pursue when addressing a particular detected analyte.

As shown in FIGS. 3A-D, projected analyte indicator 300A includes perimeter 350 (e.g., an analyte indicator structure) configured to indicate presence and spatial extents of a detected analyte, projected analyte indicator 300B includes intensity or false color graph 352 configured to additionally indicate an estimate of the concentration of an analyte within the spatial extents and/or a mixture of different analytes within the spatial extents, projected analyte indicator 300C includes caution indicator 354 configured to indicate a particularly harmful or poisonous or mobile analyte (e.g., such as a gaseous analyte), and projected analyte indicator 300D includes textual indicator 356 configured to indicate a detected attribute of the analyte or associated environmental conditions, such as an analyte name or chemical formula, analyte concentration, length of time detected, and/or other characteristics of the detected analyte and/or the detection process.

In various embodiments, other analyte indicator shapes and combinations of indicator structures are contemplated. For example, system 101 may be configured to project perimeter 350 for a later detected time, size, and shape of an analyte, and system 101 may be configured to project, as an overlay, caution indicator 354 to indicate an earlier detected time, size, and shape of the analyte, to indicate a time evolution, for example. In some embodiments, perimeter 350 may be selected to be a circle regardless of the actual spatial extents of the detected analyte, for example, and the diameter of the circle may roughly correspond to a largest diameter of the spatial extents of the detected analyte. In general, any shape, size, text, false color mapping, shading mapping, caution fill design, and/or other standard or custom indicator structure may be used in place of or in combination with the indicator structures shown in FIGS. 3A-D.

In addition, any of analyte indicator structures 350-356 and/or other analyte indicator structures may be used in an entertainment system or decorative lighting, such as in a restaurant or dance club, for example, to indicate presence, spatial extents, and/or temperature of analytes in the form of dancers, their clothing, hot, warm, or cold flowing water, type and/or temperature of hot or cold drinks (e.g., indicating coffee, tea, water, beer, liquor, and/or their respective temperatures). In one embodiment, system 101 may be used to indicate presence of grease on an electrical cooktop and/or a temperature of the grease or the electrical cooktop.

Figure 4:
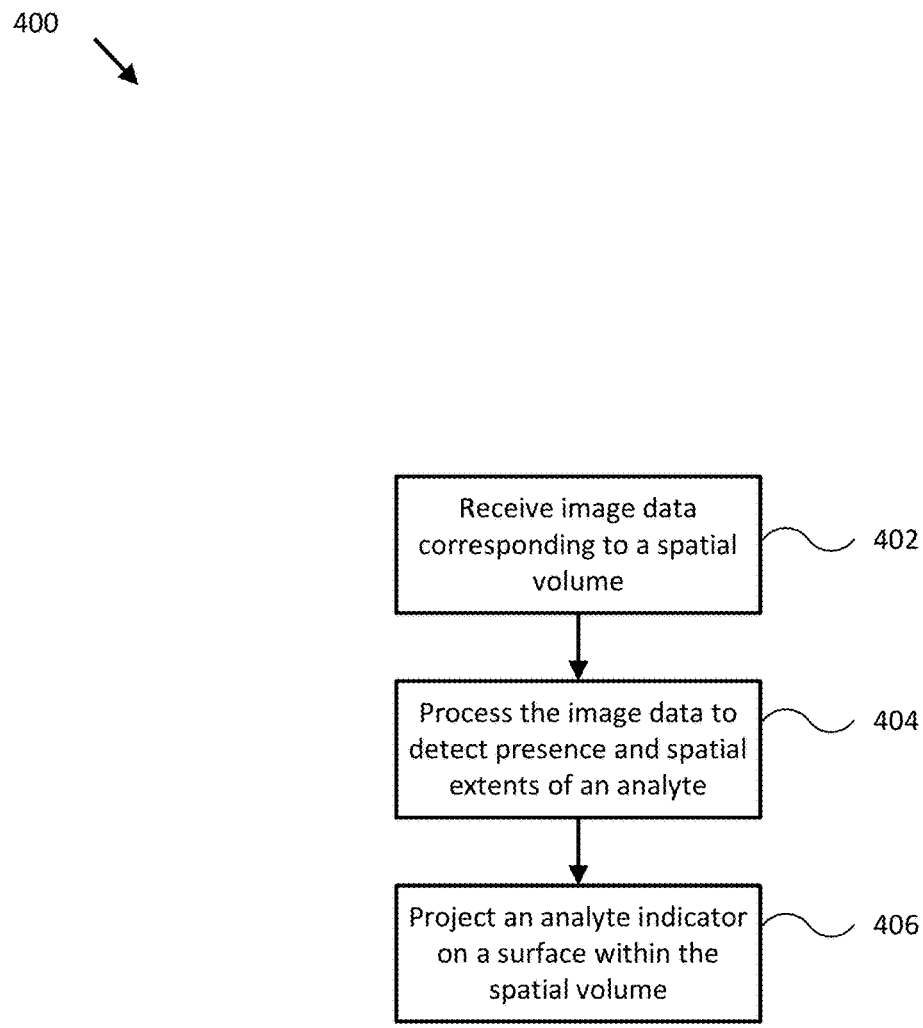
FIG. 4 illustrates a flow diagram of various operations to operate an analyte spatial detection system in accordance with an embodiment of the disclosure.

FIG. 4 illustrates a flow diagram of a process 400 to provide analyte spatial detection in accordance with an embodiment of the disclosure. In some embodiments, the operations of FIG. 4 may be implemented as software instructions executed by one or more logic devices associated with corresponding electronic devices, sensors, and/or structures depicted in FIGS. 1 through 3D. More generally, the operations of FIG. 4 may be implemented with any combination of software instructions and/or electronic hardware (e.g., inductors, capacitors, amplifiers, actuators, or other analog and/or digital components).

It should be appreciated that any step, sub-step, sub-process, or block of process 400 may be performed in an order or arrangement different from the embodiments illustrated by FIG. 4. For example, in other embodiments, one or more blocks may be omitted from or other blocks included in the process. Furthermore, block inputs, block outputs, various sensor signals, sensor information, calibration parameters, and/or other operational parameters may be stored to one or more memories prior to moving to a following portion of a corresponding process. Although process 400 is described with reference to system 101 and FIGS. 1-3D, process 400 may be performed by other systems different from those systems and including a different selection of electronic devices, sensors, assemblies, and/or system attributes.

Process 400 represents a method for providing analyte spatial detection using system 101 in accordance with embodiments of the disclosure. At the initiation of process 400, various system parameters may be populated by prior execution of a process similar to process 400, for example, or may be initialized to zero and/or one or more values corresponding to typical, stored, and/or learned values derived from past operation of process 400, as described herein.

In block 402, a logic device receives image data corresponding to a spatial volume. For example, controller 130 may be configured to control imaging module 110 to receive image data corresponding a spatial volume imaged by imaging module 110 (e.g., corresponding to a lower portion of diagrams 200A-C). In some embodiments, at least one selected spectrum for imaging module 110 includes infrared. In such embodiment, controller 130 may be configured to determine a temperature of the analyte within the spatial extents of the analyte and control visible light projector 120 to project an analyte indicator configured to indicate the temperature of the analyte within the spatial extents of the analyte. In other embodiments, at least one selected spectrum for imaging module 110 includes visible light. In such embodiment, controller 130 may be configured to receive image data corresponding to the projected analyte indicator, compare spatial extents of the projected analyte indicator to the spatial extents of the of the analyte, and determine a compensation calibration to correct errors between the spatial extents of the projected analyte indicator and the spatial extents of the of the analyte.

In block 404, a logic device processes the image data to detect a presence and spatial extents of an analyte. For example, controller 130 may be configured to process the received image data to detect a presence, spatial extents, composition, temperature, and/or other characteristics of an analyte within the spatial volume. In some embodiments, controller 130 may be configured to detect environmental characteristics associated with the detection of the analyte.

In block 406, a logic device projects an analyte indicator on a surface within the spatial volume. For example, controller 130 may be configured to control visible light projector 120 to project analyte indicator with indicator structures similar to those presented in FIGS. 3A-D, on a surface within the spatial volume, where the projected analyte indicator is configured to indicate the spatial extents of the analyte. In some embodiments, visible light projector 120 may be implemented as a variable-hue light bulb and the spatial extents may be indicated through a diffuse light that simply indicates presence within the spatial volume (e.g., the spatial extents are substantially the extents of the special volume monitored by imaging module 110). In other embodiments, visible light projector 120 may be implemented as a scanning light projector and/or a digital projector, and the spatial extents may be indicated using a general circle, for example, or more specifically using a perimeter (e.g., perimeter 350 of FIG. 3A). More generally, the projected analyte indicator may include a perimeter of the spatial extents of the analyte, a caution indicator, a textual indicator, an intensity and/or false color graph, and/or other indicator structure.

In some embodiments, imaging module 110 and visible light projector 120 may form a monolithic installation such that positions and/or orientations of imaging module 110 and visible light projector 120 are fixed relative to the spatial volume (e.g., similar to the embodiment shown in FIG. 2A).

In other embodiments, where, for example, one or both imaging module 110 and visible light projector 120 are mobile/portable, system 101 may be implemented with position and/or orientation sensors (e.g., sensors 140-146) to measure respective positions of imaging module 110 and visible light projector 120. In such embodiments, imaging module 110 and visible light projector 120 may form a distributed installation such that respective positions and/or orientations of imaging module 110 and visible light projector 120 are variable relative to each other and/or to the spatial volume (e.g., similar to the embodiment shown in FIG. 2B). Controller 130 may be configured to receive the respective positions and/or orientations of imaging module 10 and/or visible light projector 120 from the position and/or orientation sensors and control visible light projector 120 to project the analyte indicator on the surface so as to account for the respective positions and/or orientations of imaging module 110 and/or visible light projector 120 to each other and/or to the monitored spatial volume.

In further embodiments, where, for example, imaging module 110 and visible light projector 120 are integrated with each other and are mobile/portable, system 101 may be implemented with a position and/or orientation sensor (e.g., sensors 140-146) to measure respective positions of imaging module 110 and visible light projector 120 (e.g., essentially the same orientation and position, but offset from each other). In such embodiments, imaging module 110 and visible light projector 120 may form a monolithic installation such that the respective positions and/or orientations of imaging module 110 and visible light projector 120 are fixed relative to each other and variable relative to the spatial volume (e.g., similar to the embodiment shown in FIG. 2C). Controller 130 may be configured to receive the respective positions and/or orientations of imaging module 10 and visible light projector 120 from the position and/or orientation sensor and control visible light projector 120 to project the analyte indicator on the surface so as to account for the respective positions and/or orientations of imaging module 110 and visible light projector 120 relative to the monitored spatial volume.

In additional embodiments, where system 101 is implemented with communications module 132, controller 130 may be configured to control communication module 132 to transmit an electronic notification to a user interface (e.g., other modules 180) indicating the presence, composition, temperature, and/or other characteristics of the detected analyte and/or the detection process. Standardized libraries or guides of information related to the detected analyte and/or the detection process (e.g., NIOSH guides for Chemical Hazards, and/or other libraries or guides) may be transmitted to a user interface for display by a user. As noted herein, such standardized libraries and/or guides may include detailed and/or contextualized (e.g., for different environmental conditions) clean up, safety, and/or other mitigation strategies corresponding to a detected analyte, for example. By incorporating such standardized libraries and/or guides, embodiments allow users to make quicker decisions about which detection processes to use and/or mitigation strategies to pursue when addressing a particular detected analyte. Embodiments of such systems may be combined to form an array of systems 101, for example, and controller 130 may be configured to control its respective communication module 132 to communicate with the array to coordinate monitoring multiple differentiated spatial volumes substantially simultaneously, as described herein.

It is contemplated that any one or combination of methods to provide analyte spatial detection may be performed according to one or more operating contexts of a control loop, for example, such as a startup, learning, running, and/or other type operating context. For example, process 400 may proceed back to block 402 and proceed through process 400 again to produce updated image data and/or analyte detection characteristics, as in a control loop.

Embodiments of the present disclosure can thus provide direct, substantially real time, reliable, and accurate analyte spatial detection systems and/or corresponding indications to people within sight of the detected analytes. Such embodiments may be used to provide warning and analyte spatial extents sufficiently accurate to assist in efficiently and safely evacuating people from the area or to assist members of the public and otherwise non-expert workers in avoiding an otherwise dangerous and potentially invisible analyte presence.

Where applicable, various embodiments provided by the present disclosure can be implemented using hardware, software, or combinations of hardware and software. Also where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as non-transitory instructions, program code, and/or data, can be stored on one or more non-transitory machine readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the invention. Accordingly, the scope of the invention is defined only by the following claims.

What is claimed is:

1. A system comprising:
an imaging module configured to image a spatial volume for electromagnetic radiation in at least one selected spectrum;
a visible light projector configured to generate visible light and project it within the spatial volume;
one or more position and/or orientation sensors configured to measure respective positions and/or orientations of the imaging module and/or the visible light projector; and
a logic device configured to communicate with the imaging module and the visible light projector, wherein the logic device is configured to:
receive the respective positions and/or orientations of the imaging module and/or the visible light projector from the position and/or orientation sensors;
receive image data corresponding to the spatial volume from the imaging module;
process the received image data to detect a presence and spatial extents of an analyte within the spatial volume; and
control the visible light projector to project an analyte indicator on a surface within the spatial volume so as to account for the respective positions and/or orientations of the imaging module and/or the visible light projector, wherein the projected analyte indicator is configured to indicate the spatial extents of the analyte.

2. The system of claim 1, wherein:
the at least one selected spectrum comprises infrared;
the surface comprises an object surface within the spatial volume and/or an analyte surface of the analyte;
the analyte indicator is configured to indicate a physical property of the analyte within the spatial extents of the analyte and/or a method for decontaminating the spatial volume of the analyte; and
the physical property of the analyte comprises a temperature, a composition, a chemical class, and/or a toxicity of the analyte.

3. The system of claim 1, wherein:
the at least one selected spectrum comprises visible light; and
the logic device is configured to:
receive image data corresponding to the projected analyte indicator;
compare spatial extents of the projected analyte indicator to the spatial extents of the of the analyte; and
determine a compensation calibration to correct errors between the spatial extents of the projected analyte indicator and the spatial extents of the analyte.

4. The system of claim 1, wherein:
the visible light projector comprises a scanning light projector; and
the projected analyte indicator comprises a perimeter of the spatial extents of the analyte, a caution indicator, and/or a textual indicator.

5. The system of claim 1, wherein:
the visible light projector comprises a digital projector; and
the projected analyte indicator comprises an intensity and/or false color graph.

6. The system of claim 1, wherein:
the imaging module and the visible light projector form a monolithic installation such that positions and/or orientations of the imaging module and the visible light projector are fixed relative to the spatial volume; and
the analyte comprises a solid, liquid, or gas disposed within the spatial volume.

7. The system of claim 1, wherein:
the imaging module and the visible light projector form a distributed installation such that the respective positions and/or orientations of the imaging module and the visible light projector are variable relative to each other.

8. The system of claim 1, wherein:
the imaging module and the visible light projector form a monolithic installation such that the respective positions and/or orientations of the imaging module and the visible light projector are fixed relative to each other and variable relative to the spatial volume; and
the logic device is configured to:
control the visible light projector to project the analyte indicator on the surface so as to account for the respective positions and/or orientations of the imaging module and the visible light projector relative to the spatial volume.

9. The system of claim 1, further comprising a communication module, wherein:
the analyte comprises water, gasoline, coolant, oil, an acid, cooking gas, nitrogen, oxygen, a human-poisonous gas, an explosive, a chemical weapon, an oxidizer, and/or a toxic industrial chemical; and the logic device is configured to control the communication module to transmit an electronic notification to a user interface indicating the presence, composition, and/or temperature of the detected analyte.

10. An array of the system of claim 1, wherein:

each system further comprises a respective communication module;

each imaging module of the array of systems comprises one or more microbolometers, thermopiles, quantum well infrared photodetectors, InGaAs based photodetectors, HgCdTe based photodetectors, imaging Raman spectrometer assemblies, complementary metal-oxide semiconductor sensors, near infrared sensors, silicon photomultipliers, hyperspectral imagers, and/or multispectral imagers; and each logic device is configured to control the respective communication module to communicate with the array to coordinate monitoring multiple differentiated spatial volumes substantially simultaneously.

11. A method comprising:

receiving image data corresponding to a spatial volume imaged by an imaging module;

receiving respective positions and/or orientations of the imaging module and/or a visible light projector configured to generate visible light and project it within the spatial volume from one or more position and/or orientation sensors configured to measure respective positions and/or orientations of the imaging module and/or the visible light projector;

processing the received image data to detect a presence and spatial extents of an analyte within the spatial volume; and projecting an analyte indicator on a surface within the spatial volume so as to account for the respective positions and/or orientations of the imaging module and/or the visible light projector, wherein the analyte indicator is configured to indicate the spatial extents of the analyte.

12. The method of claim 11, wherein:

at least one selected spectrum for the imaging module comprises infrared; and the surface comprises an object surface within the spatial volume and/or an analyte surface of the detected analyte;

the analyte indicator is configured to indicate a physical property of the analyte within the spatial extents of the analyte and/or a method for decontaminating the spatial volume of the analyte; and the physical property of the analyte comprises a temperature, a composition, a chemical class, and/or a toxicity of the analyte.

13. The method of claim 11, wherein:

at least one selected spectrum comprises visible light; and
the method further comprises:

receiving image data corresponding to the projected analyte indicator;

comparing spatial extents of the projected analyte indicator to the spatial extents of the of the analyte; and determining a compensation calibration to correct errors between the spatial extents of the projected analyte indicator and the spatial extents of the of the analyte.

14. The method of claim 11, wherein:

the projected analyte indicator comprises a perimeter of the spatial extents of the analyte, a caution indicator, and/or a textual indicator.

15. The method of claim 11, wherein:

the projected analyte indicator comprises an intensity and/or false color graph.

16. The method of claim 11, wherein:

the imaging module and a visible light projector projecting the analyte indicator form a monolithic installation such that positions and/or orientations of the imaging module and the visible light projector are fixed relative to the spatial volume; and the analyte comprises a solid, liquid, or gas disposed within the spatial volume.

17. The method of claim 11, wherein:

the imaging module and the visible light projector projecting the analyte indicator form a distributed installation such that respective positions and/or orientations of the imaging module and the visible light projector are variable relative to each other.

18. The method of claim 11, wherein:

the imaging module and a visible light projector projecting the analyte indicator form a monolithic installation such that respective positions and/or orientations of the imaging module and the visible light projector are fixed relative to each other and variable relative to the spatial volume; and the method further comprises:

controlling the visible light projector to project the analyte indicator on the surface so as to account for the respective positions and/or orientations of the imaging module and the visible light projector relative to the spatial volume.

19. The method of claim 11, wherein:

the analyte comprises water, gasoline, coolant, oil, an acid, cooking gas, nitrogen, oxygen, a human-poisonous gas, an explosive, a chemical weapon, an oxidizer, and/or a toxic industrial chemical; and the method further comprises controlling the communication module to transmit an electronic notification to a user interface indicating the presence, composition, and/or temperature of the detected analyte.

20. The method of claim 11, further comprising:

controlling a communication module to communicate with an array of analyte spacial detection systems to coordinate monitoring multiple differentiated spatial volumes substantially simultaneously.

* * * * *